United States Patent [19]

Tanaka et al.

[11] Patent Number: 4,558,393
[45] Date of Patent: Dec. 10, 1985

[54] MOISTURE SENSOR

[75] Inventors: Junichi Tanaka, Tenri; Hisatoshi Furubayashi, Yamatokoriyama; Masanori Watanabe, Tenri; Masaya Hijikigawa, Yamatokoriyama, all of Japan

[73] Assignee: Sharp Kabushiki Kaisha, Japan

[21] Appl. No.: 604,387

[22] Filed: Apr. 27, 1984

[30] Foreign Application Priority Data

Apr. 28, 1983 [JP] Japan ................................. 58-76843

[51] Int. Cl.⁴ .............................................. H01G 5/20
[52] U.S. Cl. ................................................. 361/286
[58] Field of Search ........................... 324/60 R, 61 R; 361/323, 286, 304

[56] References Cited

U.S. PATENT DOCUMENTS

| | | |
|---|---|---|
| 2,297,346 | 9/1942 | Crist .................................. 324/61 R |
| 2,703,857 | 3/1955 | Engelhardt et al. ................ 361/323 |
| 3,350,941 | 11/1967 | Misevich et al. ............... 361/286 X |
| 4,164,868 | 8/1979 | Suntola ........................... 361/286 X |
| 4,393,434 | 7/1983 | Imai et al. ........................... 361/286 |

FOREIGN PATENT DOCUMENTS 99058  7/1980  Japan .................................. 361/286

Primary Examiner—Donald A. Griffin
Attorney, Agent, or Firm—Keil & Weinkauf

[57] ABSTRACT

A moisture sensor comprising a substrate, a moisture sensitive polymer film having hydroxyl groups formed on said substrate, an electrode formed on said moisture sensitive film, and a chemical modification layer disposed between said substrate and said moisture sensitive film, said chemical modification layer having chemical bonding strength to both said substrate and said moisture sensitive film thereby increasing adhesion between said substrate and said moisture sensitive film.

4 Claims, 2 Drawing Figures

MOISTURE SENSOR

BACKGROUND OF THE INVENTION

1. Field of the Invention

The present invention relates to a moisture sensor comprising a substrate, an electrode and a moisture sensitive polymer film. More particularly, it relates to a moisture sensor wherein the moisture sensitive polymer film is tightly bound to the substrate to ensure a stable and reproducible moisture sensitive characteristic.

2. Description of the Prior Art

It has been known that a moisture sensor having a polymer film formed on a substrate can detect humidity in the atmosphere due to variation of the electrostatic capacity of the polymer film. However, the polymer film materials have little affinity for the substrate resulting in the lack of adhesion to the substrate, so that an accurate electric signal is not obtainable from such a conventional moisture sensor.

FIG. 1 shows a structure of a typical moisture sensor having an organic polymer film, wherein on a substrate 1 made of an insulator such as a metal oxide, glass or the like, a moisture sensitive film 2 made of an organic polymer is formed and a moisture permeable electrode 3 is further formed on the moisture sensitive polymer film 2. The moisture sensor detects variation of humidity in the atmosphere as variation of an impedance depending on variation of the electrostatic capacity of the organic polymer film.

The organic polymer film is generally formed on the substrate in such a manner that an organic polymer solution which is prepared by dissolving an organic polymer in a solvent is coated on the substrate by a spin casting technique or an immersion technique followed by a baking treatment or a drying treatment to form a moisture sensitive film. Alternatively, the moisture sensitive film is directly formed on the substrate or the electrode by a spattering technique or a plasma CVD technique. However, the resulting moisture sensitive film has insufficient adhesion to the substrate, resulting in an unstable impedance and/or an apparent aged deterioration of the moisture sensitive characteristic (humidity/impedance characteristic) thereof. This is most easily observed when the moisture sensitive film is formed by a spin casting technique or an immersion technique. It is presumed that the moisture sensitive film materials do not have strong chemical bonding strength to the substrate materials and that a swelling and/or a shrinkage occurs in the moisture sensitive film depending upon the amount of water absorbed in the film, namely humidity in the atmosphere, thereby further weakening the adhesion between the film and the substrate.

SUMMARY OF THE INVENTION

The moisture sensor of this invention which overcomes the above-discussed disadvantages of the prior art, comprises a substrate, a moisture sensitive polymer film having hydroxyl groups formed on said substrate, an electrode formed on said moisture sensitive film, and a chemical modification layer disposed between said substrate and said moisture sensitive film, said chemical modification layer having chemical bonding strength to both said substrate and said moisture sensitive film thereby increasing adhesion between said substrate and said moisture sensitive film.

The chemical modification layer contains a silylating reagent having epoxy groups.

The silylating reagent is at least one selected from the group consisting of the following compounds:

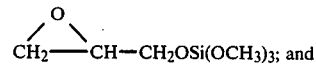

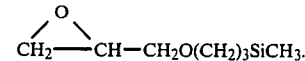

The polymer forming the moisture sensitive film is preferably polyvinyl alcohol.

Thus, the invention described herein makes possible the objects of providing a novel and useful moisture sensor wherein a chemical modification layer is disposed between a substrate and a moisture sensitive film made of polyvinyl alcohol to tightly adhere the film to the substrate; and providing a moisture sensor which ensures a stable operation.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

The arrangement, function and effects of the invention will now be described with reference to the drawings showing embodiments of the invention. The following illustrates the most typical examples, but it is to be understood that these are not intended to limit the scope of the invention and that changes and modifications thereof are within the technical scope of the invention.

By a vacuum evaporation technique, a spattering technique or the like, a conductive metal film is formed on a base made of an insulator such as glass or alumina, or a semiconductor such as silicone, with the formation of a substrate. Alternatively, a metal board may be used as a substrate.

On the resulting substrate, a 10% ethanol solution of a silylating reagent represented by the chemical formula:

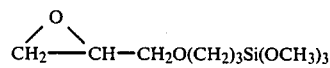

is coated by a spin casting method and dried at 90° C. to bind the silylating reagent to the substrate, which is then coated with an aqueous solution of polyvinyl alcohol as a moisture sensitive film material and dried by a ventilation process, followed by a heat treatment to bind the moisture sensitive film to the substrate resulting in a moisture sensitive film on the substrate. Finally, an electrode is disposed on the moisture sensitive film.

The mechanism of fixation of the polymer film to the substrate may be explained as follows:

The conductive metal film constituting the substrate has hydroxyl groups on its surface which react with the silylating reagent as follows:

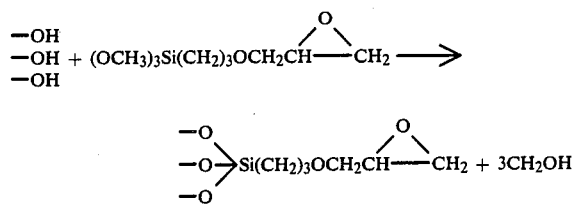

Hydroxyl groups contained in polyvinyl alcohol react with the silylating reagent as follows:

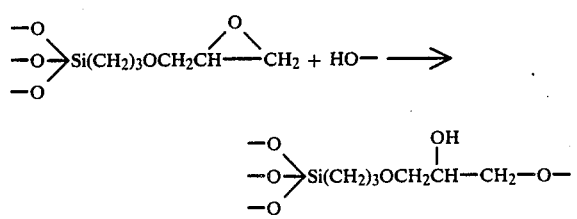

Figure 1:
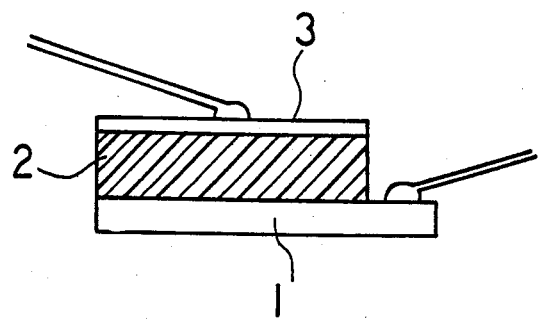
FIG. 1 is a partly sectional view of a basic structure of a moisture sensor.
Figure 2:
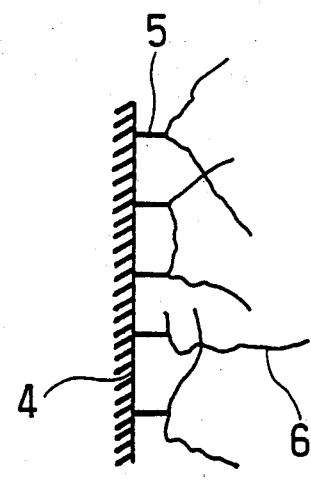
FIG. 2 is a scheme illustrating the moisture sensor of this invention.

A scheme for the resulting moisture sensitive film is shown in FIG. 2, illustrating that polyvinyl alcohol 6 binds with the silylating reagent 5 on the substrate 4. Thus, by the use of this chemical modification layer, the moisture sensitive film is tightly bound to the substrate.

Even though the moisture sensor having the moisture sensitive film which is fixed to the substrate according to this invention is allowed to stand in hot water, the moisture sensitive film will not be eluted due to the hot water and the moisture sensitive characteristic of the film will be stably maintained. However, when a moisture sensor having a moisture sensitive film which is not fixed to the substrate as described in this invention is allowed to stand in hot water, it will be observed that the moisture sensitive film will peel from the substrate.

According to this invention, the preferred example of polymer to be used as a material for the moisture sensitive film is polyvinyl alcohol. Other examples thereof are known polymer having hydroxyl groups such as hydroxyalkylpolyacrylate.

An alternative to the above-mentioned moisture sensor which is constituted in such that the moisture sensitive film is disposed between the substrate and the electrode thereby allowing for the detection of a variation in the impedance from both surfaces of the moisture sensitive film, would be a moisture sensor having a pair of comb-shaped electrodes which are disposed on the insulative substrate, the moisture sensitive film being formed on the electrodes, and the chemical modification layer being formed between the moisture sensitive film and the substrate and between the moisture sensitive film and the electrodes thereby allowing for the detection of a variation in the impedance of the moisture film.

Further examples of the silylating reagent are compounds represented by the chemical formulas:

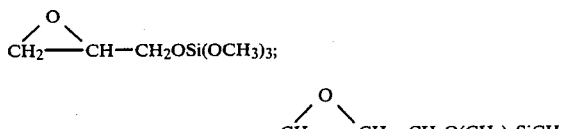

or the like, in addition to the afore-mentioned compound,

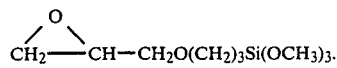

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A moisture sensor comprising a substrate, a moisture sensitive polymer film having hydroxyl groups formed on said substrate, an electrode formed on said moisture sensitive film, and a chemical modification layer disposed between said substrate and said moisture sensitive film, said chemical modification layer having chemical bonding strength to both said substrate and said moisture sensitive film thereby increasing adhesion between said substrate and said moisture sensitive film, said chemical modification layer containing a silylating reagent having epoxy groups.

2. A moisture sensor according to claim 1, wherein said silylating reagent is at least one selected from the group consisting of the following compounds:

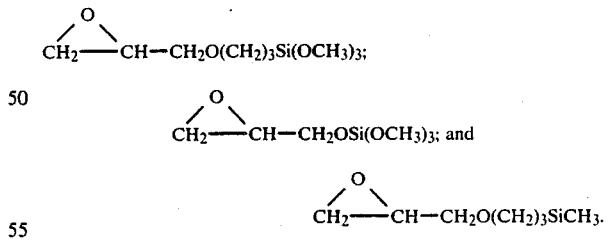

3. A moisture sensor according to claim 2, wherein said polymer forming the moisture sensitive film is polyvinyl alcohol.

4. A moisture sensor according to claim 1, wherein said polymer forming the moisture sensitive film is polyvinyl alcohol.

* * * * *